(12) United States Patent
Jungwirth (10) Patent No.: US 9,134,174 B2
(45) Date of Patent: Sep. 15, 2015

(54) LASER DETECTION AND WARNING SYSTEM

(71) Applicant: The Boeing Company, Chicago, IL (US)

(72) Inventor: Douglas R. Jungwirth, Porter Ranch, CA (US)

(73) Assignee: The Boeing Company, Chicago, IL (US)

( * ) Notice: Subject to any disclaimer, the term of this patent is extended or adjusted under 35 U.S.C. 154(b) by 217 days.

(21) Appl. No.: 13/735,889

(22) Filed: Jan. 7, 2013

(65) Prior Publication Data

US 2014/0192367 A1 Jul. 10, 2014

(51) Int. Cl.

| G01B 11/26 | (2006.01) |
|---|---|
| G01C 1/00 | (2006.01) |
| G01B 11/14 | (2006.01) |
| G01J 1/44 | (2006.01) |
| G01S 7/495 | (2006.01) |
| F41H 13/00 | (2006.01) |
| G01S 7/48 | (2006.01) |
| G01J 3/50 | (2006.01) |
| G01J 3/51 | (2006.01) |
| G01S 7/00 | (2006.01) |
| A61F 9/02 | (2006.01) |

(52) U.S. Cl.
CPC . *G01J 1/44* (2013.01); *F41H 13/00* (2013.01); *G01B 11/14* (2013.01); *G01J 3/50* (2013.01); *G01J 3/51* (2013.01); *G01S 7/4804* (2013.01); *G01S 7/495* (2013.01); *A61F 9/022* (2013.01); *G01S 7/003* (2013.01)

(58) Field of Classification Search
CPC ......... G01S 17/02; G01S 17/06; G01S 17/66; G01S 7/4804
See application file for complete search history.

(56) References Cited

U.S. PATENT DOCUMENTS

| 3,203,305 A | 8/1965 | Fairbanks |
|---|---|---|
| 3,610,755 A | 10/1971 | Wieberger et al. |
| 3,802,780 A | 4/1974 | Helm et al. |
| 3,924,232 A * | 12/1975 | Burdi et al. ..................... 342/54 |

(Continued)

FOREIGN PATENT DOCUMENTS

| WO | 92/15024 | 9/1992 |
|---|---|---|
| WO | WO 9215024 A1 * | 9/1992 |
| WO | 2012/093399 | 7/2012 |

OTHER PUBLICATIONS http://articles.janes.com/articles/Janes-Radar-and-Electronic-Warfare-Systems/AN-AVR-2A-V2B-V-laser-detecting-set-United-States.html.

(Continued)

*Primary Examiner* — Kara E Geisel
*Assistant Examiner* — Hina F Ayub
(74) *Attorney, Agent, or Firm* — Walters & Wasylyna LLC (57) ABSTRACT

A laser detection and warning system and associated methods of warning a pilot of an aircraft of incoming laser radiation and determining a location of a source of laser radiation including a detector configured to be mounted to an aircraft, the detector having an optical subsystem, a detector subsystem, and a processor subsystem to determine characteristics of incoming laser radiation and transmit a laser warning output signal, wherein the laser warning output signal may include wavelength characteristics of the laser radiation, corresponding protective eyewear type, and location of the source of the laser radiation.

20 Claims, 9 Drawing Sheets

(56) References Cited

U.S. PATENT DOCUMENTS

| | | | |
|---|---|---|---|
| 4,277,170 | A | 7/1981 | Miles |
| 4,682,024 | A | 7/1987 | Halidorsson et al. |
| 4,721,852 | A | 1/1988 | Muller |
| 4,962,311 | A | 10/1990 | Poisel et al. |
| 5,243,179 | A | 9/1993 | Bjorkman |
| 5,440,116 | A | 8/1995 | Bolander et al. |
| 5,914,661 | A | 6/1999 | Gross |
| 6,283,756 | B1 * | 9/2001 | Danckwerth et al. ........... 434/11 |
| 7,360,703 | B2 | 4/2008 | McIntyre et al. |
| 7,683,310 | B1 * | 3/2010 | Sinclair et al. ................ 250/216 |
| 7,846,028 | B2 | 12/2010 | Small et al. |
| 2002/0179818 | A1 * | 12/2002 | Gauthier et al. .......... 250/206.1 |
| 2003/0234349 | A1 * | 12/2003 | Wootton et al. ............... 250/226 |
| 2004/0104334 | A1 * | 6/2004 | Gal et al. ................... 250/203.6 |
| 2005/0162575 | A1 * | 7/2005 | Harvie ........................... 349/16 |

OTHER PUBLICATIONS http://www.google.com/url?sa=t&rct=j&q=an%2Favr2b(v)&source=web&cd=3&cad=rja&ved=0CCkQFjAC&url=http%3A%2F%2F65.18.194.107%2F~admin1%2Fimages%2Fpdf%2F05_ASE%2F05ASE_WayneMorton.ppt&ei=hoFQULSOOtHZigLVuYEg&usg=AFQjCNG3m_smMXf1CqCMIcnTGgpIAE_I_Q.

http://www.ausa.org/publications/armymagazine/archive/2008/1/Documents/SA_0108.pdf.

http://www.atk.com/Products/documents4-1/DES%20-%20AAR-47%20HFI.pdf.

http://www.baesystems.com/cs/groups/public/documents/document/mdaw/mdm3/~edisp/baes_019640.pdf.

http://www.elisra.com/LWS_20V_3.html.

http://articles.janes.com/articles/Janes-Avionics/LWS-20-laser-warning-system-Israel.html.

https://janes.ihs.com/CustomPages/Janes/DisplayPage.aspx?DocType=Reference&ItemId=+++1339544&Pubabbrev=JAV_.

Extended European Search Report, EP 13 19 7661 (2014).

* cited by examiner

LASER DETECTION AND WARNING SYSTEM

FIELD

The present disclosure is generally related to laser warning systems and, more particularly, to an airborne laser detection and warning system and associated methods to alert a pilot of the type and direction of a laser beam and the location of a source of the laser beam.

BACKGROUND

Over the last decade there have been numerous incidents of hand-held lasers being directed at aircraft. This has become a common and dangerous occurrence for commercial pilots and news and weather helicopter pilots. While exposure to hand-held laser light under such circumstances may seem trivial due to the brevity of exposure and large distances involved, exposure to hand-held laser light under such circumstances may create dangerous conditions such as flash blindness of the pilot. If this occurs during a critical moment in aircraft operation, the aircraft may be endangered. For example, temporary blindness during a landing or certain navigation tasks may have disastrous results. Furthermore, laser light can cause temporary or permanent damage to the eye. Reliable detection and identification of the type and direction of laser radiation may be critical to pilot safety and accurate information related to the location of a source of the laser may provide for appropriate protective measures or law enforcement responses.

Additionally, military pilots are not only at risk of temporary blindness due to hand-held lasers, but are also subject to being "designated" by laser targeting. Generally in connection with military aircraft, laser detection devices register laser radiation from laser rangefinders or laser designators and by a warning signal to make clear to the designated aircraft, i.e., pilot, that laser illumination has occurred or is continuing. Reliable detection and identification of laser radiation may be critical to mission success and accurate information related to the type of laser may provide for appropriate countermeasures.

Accordingly, those skilled in the art continue with research and development efforts in the field of laser detection and warning systems.

SUMMARY

In one embodiment, the disclosed laser detection and warning system may include a detector configured to be mounted to an aircraft, the detector including an optical subsystem, a detector subsystem, and a processor subsystem to determine characteristics of incoming laser radiation and transmit a laser warning output signal, wherein the laser warning output signal includes wavelength characteristics of the laser radiation and corresponding protective eyewear type.

In another embodiment, the disclosed laser detection and warning system may include a detector configured to be mounted to an aircraft, the detector including an optical subsystem, a detector subsystem, and a processor subsystem to determine characteristics of incoming laser radiation and transmit a laser warning output signal, wherein the laser warning output signal includes wavelength characteristics of the laser radiation, corresponding protective eyewear type, direction of approach characteristics of the laser radiation, and location characteristics of a source of the laser radiation.

In another embodiment, the disclosed laser detection and warning system may include a detector configured to be mounted to an aircraft, the detector including an optical subsystem, a detector subsystem, and a processor subsystem to determine characteristics of incoming laser radiation and transmit a laser warning output signal, wherein the laser warning output signal includes wavelength characteristics of the laser radiation, corresponding protective eyewear type and direction of approach characteristics of the laser radiation.

In another embodiment, the disclosed laser detection and warning system may include a detector configured to be mounted to an aircraft, the detector including an optical subsystem, a detector subsystem, and a processor subsystem to determine characteristics of incoming laser radiation and transmit a laser warning output signal, wherein the laser warning output signal includes wavelength characteristics of the laser radiation, corresponding protective eyewear type, direction of approach characteristics of the laser radiation, and location characteristics of a source of the laser radiation.

In another embodiment, the disclosed method for warning a pilot of an aircraft of the presence of laser radiation may include the steps of: (1) providing a detector mounted to an aircraft, the detector including an optical subsystem, a detector subsystem, and a processor subsystem, (2) detecting incoming laser radiation with the optical subsystem, (3) focusing and directing the laser radiation to the detector subsystem, (4) generating a digital signal in response to the laser radiation, (5) transmitting the digital signal to the processor subsystem, (6) processing the digital signal determining wavelength characteristics of the laser radiation, and (7) transmitting a laser warning output signal including the wavelength characteristics of the laser radiation and identifying corresponding protective eyewear type.

In another embodiment, the disclosed method for warning a pilot of an aircraft of the presence of laser radiation may include the steps of: (1) providing a detector mounted to an aircraft, the detector including an optical subsystem, a detector subsystem, and a processor subsystem, (2) detecting incoming laser radiation with the optical subsystem, (3) focusing and directing the laser radiation to the detector subsystem, (4) generating a digital signal in response to the laser radiation, (5) transmitting the digital signal to the processor subsystem, (6) processing the digital signal determining wavelength characteristics of the laser radiation, (7) processing the digital signal determining a direction of approach of the laser radiation, and (8) transmitting a laser warning output signal including the wavelength characteristics of the laser radiation, identifying corresponding protective eyewear type, and the direction of approach of the laser radiation.

In another embodiment, the disclosed method for determining a location of a source of laser radiation may include the steps of: (1) providing a detector mounted to an aircraft, the detector including an optical subsystem, a detector subsystem, and a processor subsystem, (2) detecting incoming laser radiation with the optical subsystem, (3) focusing and directing the laser radiation to the detector subsystem, generating a digital signal in response to the laser radiation, (4) transmitting the digital signal to the processor subsystem, (5) processing the digital signal determining intensity characteristics of the laser radiation, (6) processing the digital signal determining direction of approach characteristics of the laser radiation, (7) determining a spatial position of the aircraft, (8) correlating the digital signals and the position of the aircraft, (9) calculating a distance and direction of a source of the laser radiation relative to the spatial position of the aircraft, and (10) transmitting a laser warning output signal including a location of the source of the laser radiation.

Other aspects of the disclosed laser detection and warning system will become apparent from the following detailed description, the accompanying drawings and the appended claims.

DETAILED DESCRIPTION

The following detailed description refers to the accompanying drawings, which illustrate specific embodiments of the disclosure. Other embodiments having different structures and operations do not depart from the scope of the present disclosure. Like reference numerals may refer to the same element or component in the different drawings.

Although the disclosed laser detection and warning system and related methods discussed below are discussed primarily in terms of use for detecting laser light directed at an aircraft, and particularly a cockpit of an aircraft, it may be appreciated by one skilled in the art that the system and methods herein disclosed may be used for any type of laser detection, such as detecting a laser being used to illuminate, i.e., designate, an air or land vehicle in a combat situation. Further, it may be appreciated by one skilled in the art that while the system and methods below relate to detecting laser light, the system may be used to detect any type of illumination from any type of source, regardless of the wavelength. It may further be appreciated that the detection of the type, distance, direction, and location of the source of various types of illumination (whether or not laser light) may be useful in numerous other situations outside of commercial, civilian, or military aircrafts.

Figure 1:
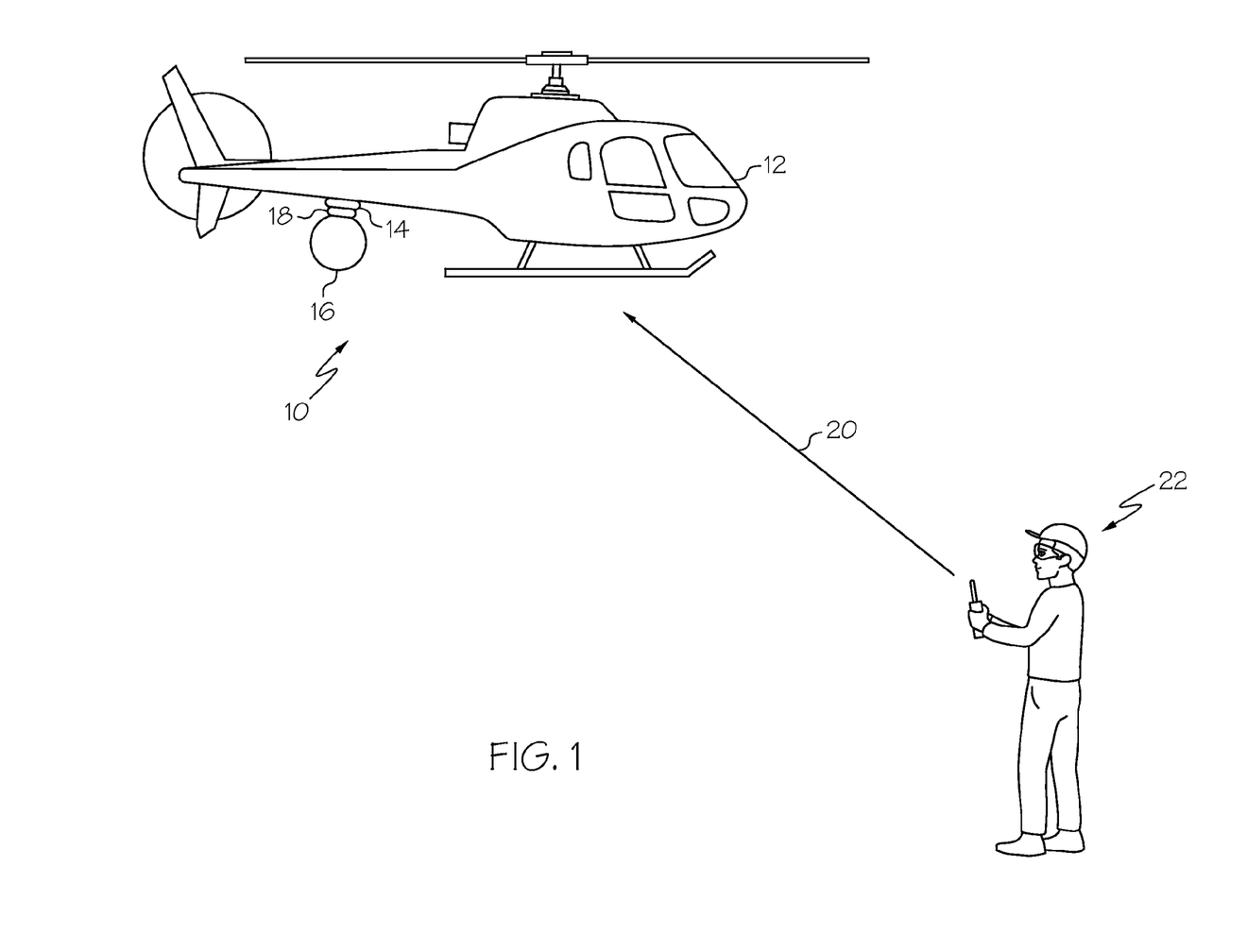
FIG. 1 is a schematic representation of one embodiment of the disclosed laser detection and warning system.

Referring to FIG. 1, an airborne laser detection and warning system, generally designated as "system" 10, may include various integrated individual aircraft platforms (identified generally as "aircraft" 12). In the illustrated embodiment, the system 10 may be mounted to a convenient location on an outside surface of the aircraft 12. In the embodiment illustrated in FIG. 1, the dimensions of the system 10 are exaggerated for ease of illustration. Alternatively, the system 10 may be integrated into the frame or fuselage of the aircraft 12. The system 10 may be suitably mounted to a stabilizer 14 of the aircraft 12. The system 10 may include a dome or head 16 supported by a base 18 mounted to the stabilizer 14. The head 16 may provide for a three hundred and sixty degree (360°) field of view (FOV), in order to fully cover a potential area where a laser beam 20 may enter a cockpit of the aircraft 12. In certain embodiments of the disclosed system 10, the head 16 may be capable of a complete rotation about a vertical axis and may be rotatably supported by a suitable bearing within the base 18.

The system 10 may detect the presence of any continuing or pulsing laser beam 20 (generally laser beam 20 may include any visible or non-visible light or other electromagnetic radiation generated by a laser) and provide several output signals to the pilot of the aircraft 12. For example, the system 10 may detect the direction of the source 22 of the laser beam 20 to indicate the direction of the incoming laser 20, i.e., the direction the pilot should not look. The system 10 may also detect the type of laser beam 20, i.e., the wavelength of the laser beam 20, and transmit such laser-type information to the pilot along with the type of safety eyewear needed to protect the pilot's eyes from damage. The system 10 may also calculate the position of the source 22 of the laser beam 20, i.e., the distance and direction of the source 22 relative to the aircraft 12, whether the source 22 is on the ground or in the air. Such location information may be transmitted to local law enforcement, in connection with civilian or commercial flights. Such information may also be transmitted to the pilot in order to perform countermeasures or to destroy the source 22, in connection with military operations.

Figure 2:
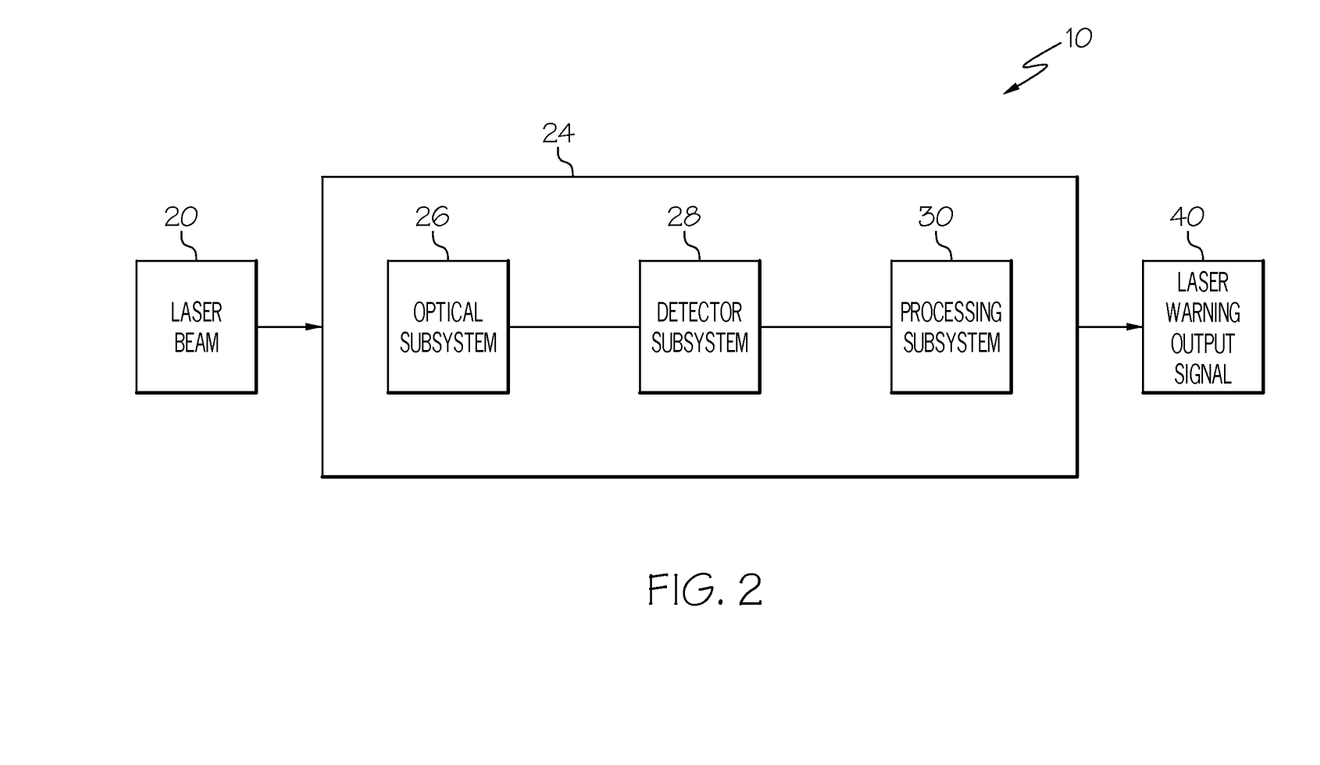
FIG. 2 is a schematic block diagram of one embodiment of a detector of the disclosed laser detection and warning system.
Figure 7:
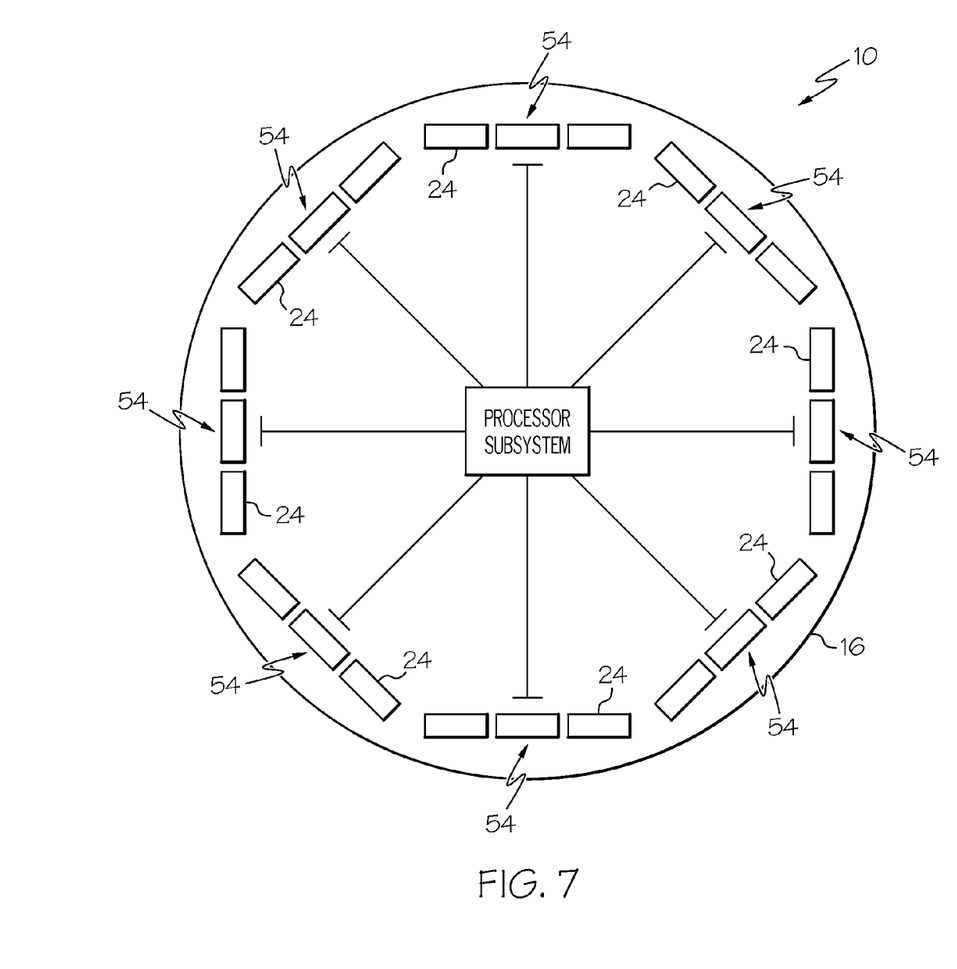
FIG. 7 is a schematic representation of another embodiment of the disclosed laser detection and warning system.

Referring next to FIG. 2, an embodiment of the disclosed system 10 may include at least one position sensitive light detector 24 or an arrangement of an array of light detectors 24 (FIG. 7). In an example embodiment, the detector 24 may include an optical subsystem 26, a detector subsystem 28, and a processing subsystem 30. The optical subsystem 26 may collect light through the head 16 (see FIG. 1) to provide various fields of view (FOV) and direction of arrival (DOA) capability. The detector subsystem 28 may receive light focused by the optical subsystem 26 and provide digital signals in response to laser beam 20. The processor subsystem 30 may receive and process the digital signals from the detector subsystem 28 and transmit a laser warning output signal 40. The laser warning output signal 40 may include audible information, visual information, or audio-visual information to the pilot.

Figure 3:
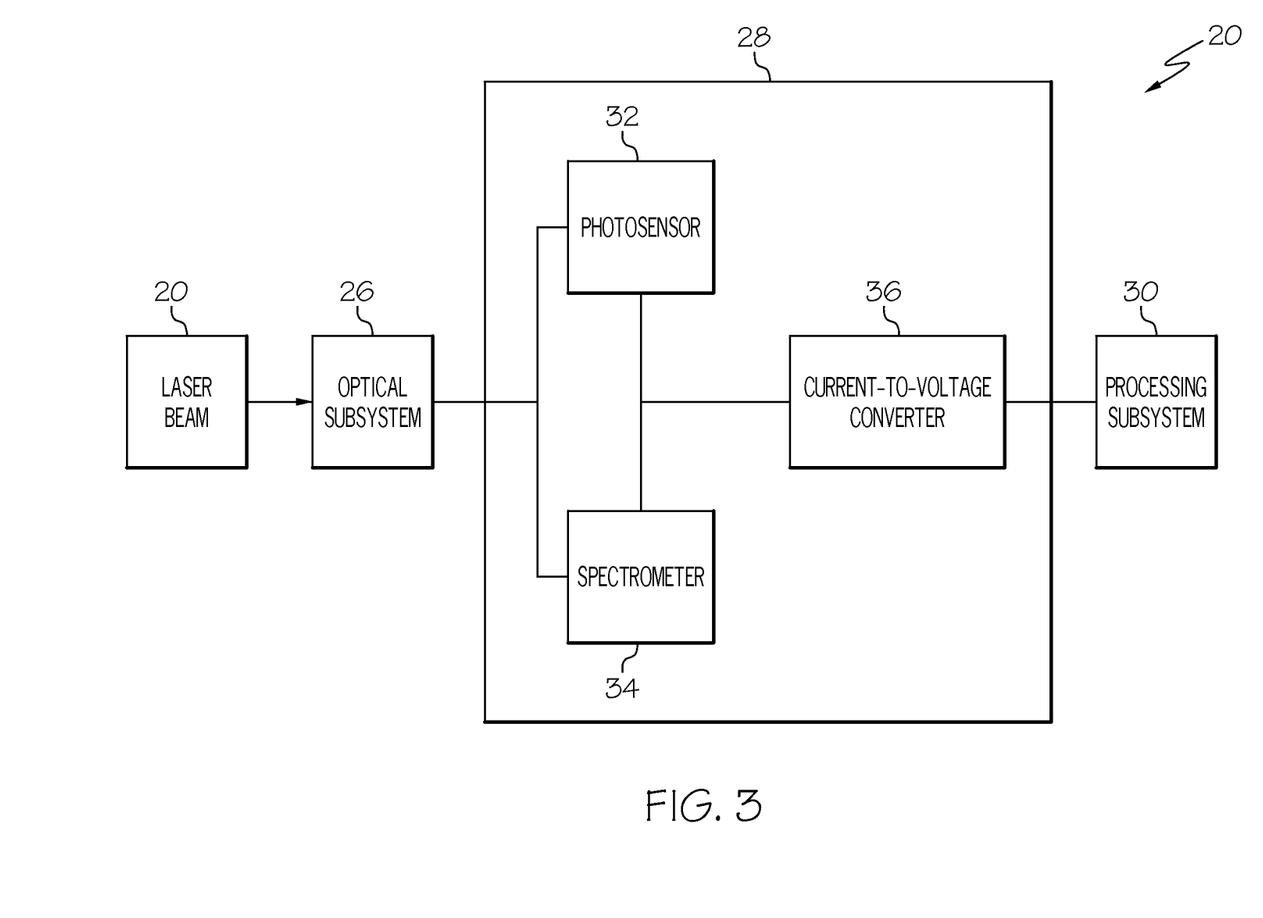
FIG. 3 is a schematic block diagram of one embodiment of a detector subsystem of the detector of the disclosed laser detection and warning system.

The array of detectors 24 may employ various techniques to detect a potential laser beam 20. Referring to FIG. 3, in one embodiment, the detector subsystem 28 may include a photosensor 32. The photosensor 32 may be any device that generates an electronic signal in response to the laser beam 20. For example, the photosensor 32 may be a photodiode or similar photodetector, which may convert light into current by creating free electrons in response to photon interactions. The detector 24 may also include a spectrometer 34 to determine wavelength of the beam 20 and a current-to-voltage converter 36 or transimpedance amplifier coupled to or otherwise in communication with the photosensor 32 to convert the current generated by the photosensor 32 into a voltage signal transmitted to the processing subsystem 30.

In another embodiment, the photosensor 32 may include a charge-coupled device (CCD) with spectrally sensitive detectors to convert the energy from the laser beam 20 into digital signals that may then be processed by the processing subsystem 30. The charge-coupled device may be any device for the movement of electrical charge from within the device to an area where the charge can be manipulated, for example conversion into a digital value for processing by the processing subsystem 30 achieved by "shifting" the signals between stages within the device one at a time. The charge-coupled device may move charge between capacitive bins in the device, with the shift allowing for the transfer of charge between bins. As an example, the charge-coupled device may include n-well/p-sub photodiodes, a capacitive transimpedance amplifier, pixel scanners, and delta differencing circuits. Use of a charge-coupled device may eliminate the need for a discrete spectrometer 34 and a current-to-voltage converter 36.

Figure 4:
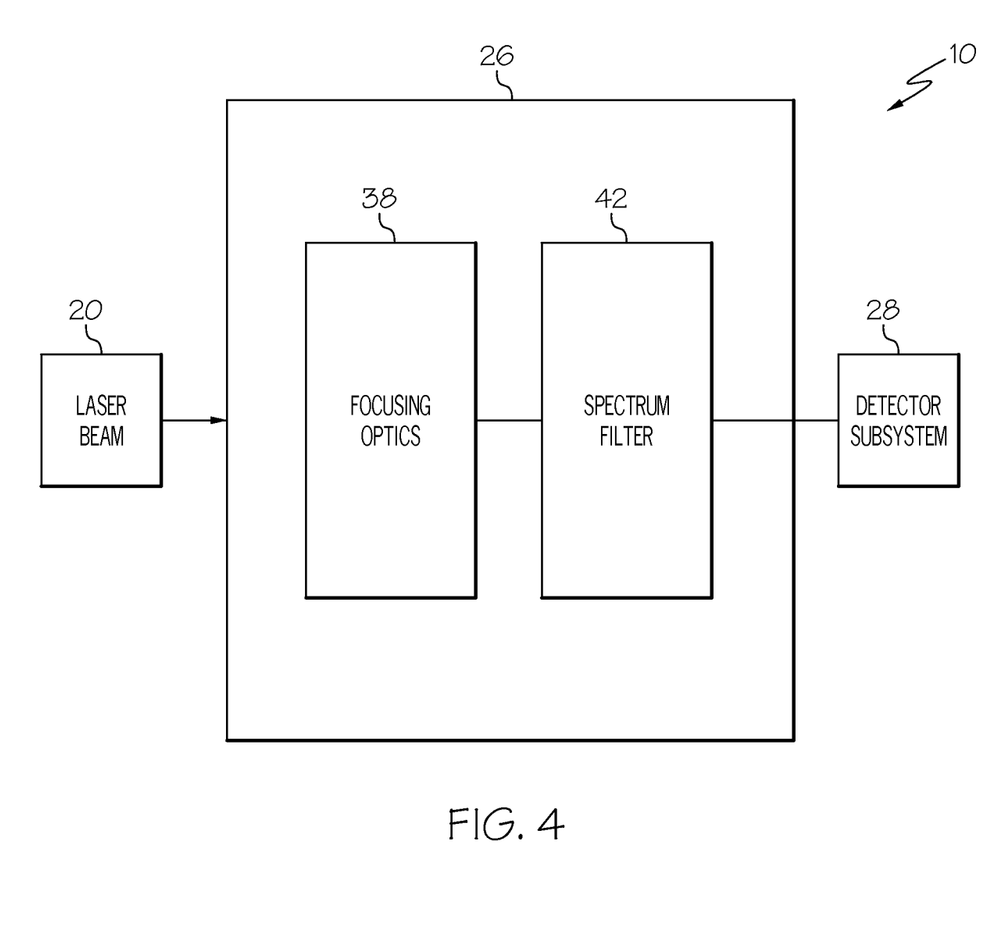
FIG. 4 is a schematic block diagram of one embodiment of an optical subsystem of the detector of the disclosed laser detection and warning system.

Referring to FIG. 4, the optical subsystem 26 may include such known components as reflectors, fiber bundles, having a plurality of fibers in an array, beam splitters, input lenses, a light control filter or other focusing optics 38. The focusing optics 38 may be an optional portion of the optical subsystem 26 used to increase the signal to background ratio of light, i.e., laser beam 20, entering the detector subsystem 28 which may help reduce false alarm situations. A spectrum filter 42 may optionally be positioned behind the focusing optics 38 to only allow light of a particular spectrum of wavelengths to reach the detector subsystem 28. In such a manner, the detector 24 may be limited to detecting light that is generally around the wavelength associated with a laser light, i.e., beam 20, in order to limit ambient light, i.e., visible light noise, before it reaches detector subsystem 28.

Figure 5:
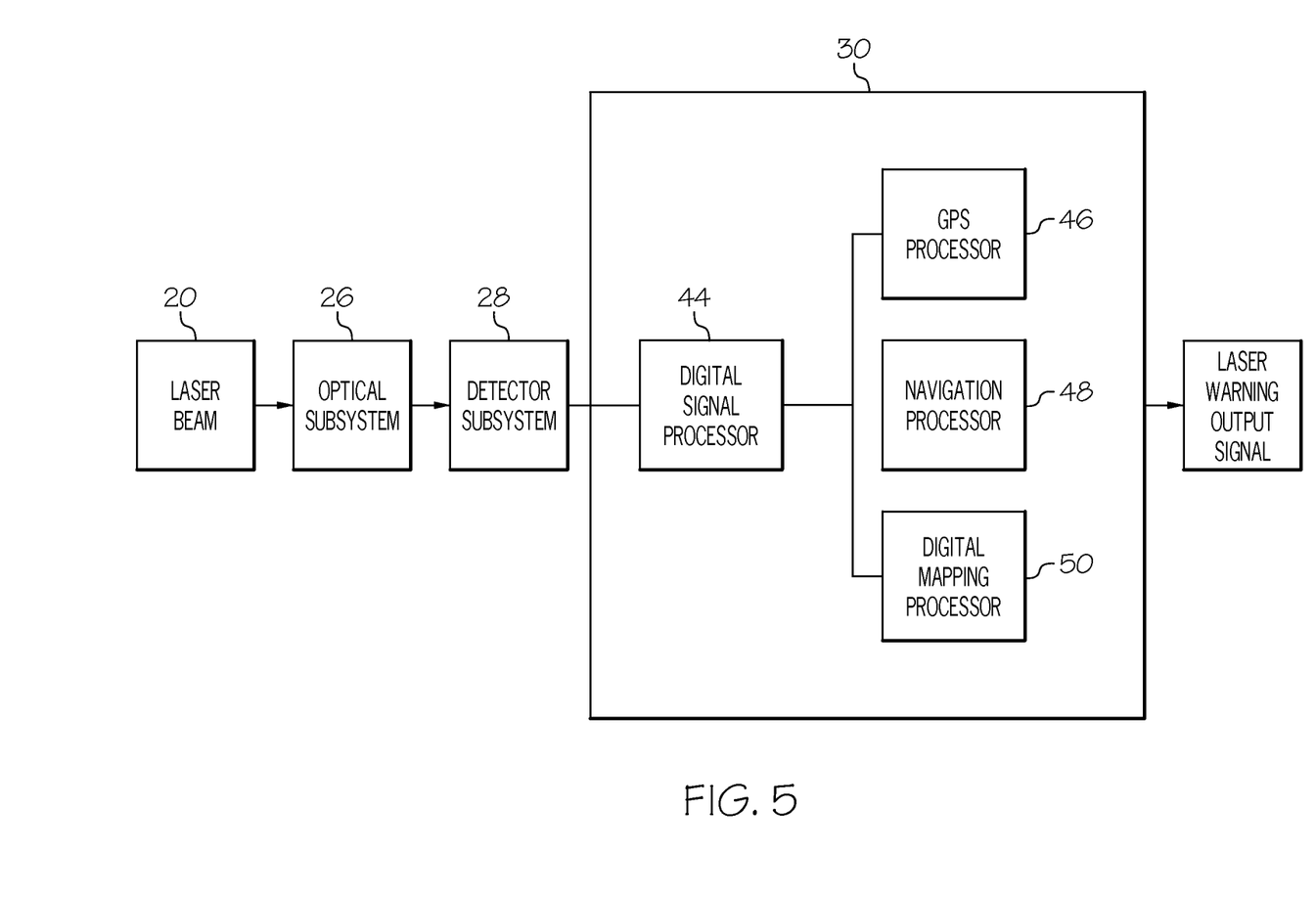
FIG. 5 is a schematic block diagram of one embodiment of a processing subsystem of the detector of the disclosed laser detection and warning system.

Referring to FIG. 5, the processing subsystem 30 may be any computer processor capable of receiving and processing the digital signal from the detector subsystem 28 and transmitting the laser warning output signal 40. For example, the processing subsystem 30 may include a digital signal processor 44 that may determine the specific type of laser beam 20, i.e., the output intensity and wavelength, based on the digital signal from the detector subsystem 28 and provide a corresponding warning output 40 to the pilot of the aircraft 12, including the appropriate type of protective eyewear needed. The digital signal processor 44 may also determine the azimuth and elevation of the source 22 of the laser beam 20 relative to the aircraft 12 based on the digital signal from the detector subsystem 28 and provide a corresponding warning output 40 to the pilot, including the direction of the incoming laser beam 20 and indication of direction on the ground or in the air the pilot should avoid looking. The processing subsystem 30 may also include a global positioning system (GPS) 46, a navigation processor 48, and a digital ground mapping processor 50 having a topographical data representation of a local area, in communication with the digital signal processor 44 to provide a corresponding warning output 40, including the exact location of the source 22 on the ground. Such location information may then be transmitted to law enforcement or other authorities for appropriate action.

Figure 6:
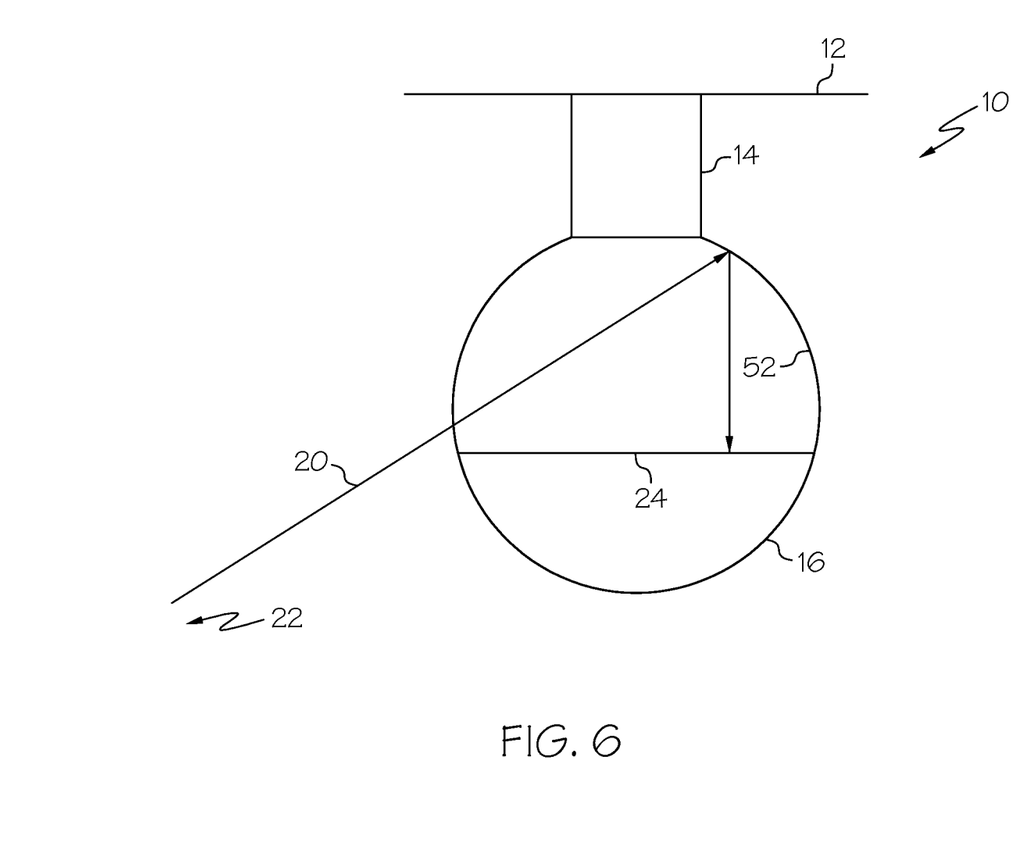
FIG. 6 is a schematic representation of another embodiment of the disclosed laser detection and warning system.

Referring to FIG. 6, in one embodiment, the optical subsystem 26 may be provided with a reflector 52, which focuses incoming laser radiation, i.e., laser beam 20, towards the detector subsystem 28. As illustrated, the reflector 52 may be integrated within the head 16. In one embodiment, the detector subsystem 28 may be an annular position sensitive photosensor 32, which is in the focus of the surrounding reflector 52. From the figure it is evident that the laser radiation 20 is focused towards an area on the detector subsystem that is diametrically opposite the one from which it comes, which consequently may be used to determine the bearing to the laser source 22.

It can be appreciated that the head 16 may include the filter 42 that may filter out undesired electromagnetic radiation of certain wavelengths in order to minimize or eliminate false alarms of the system 10. The reflector 52 may be disposed on the inner side of a head 16 above the detector subsystem 28. The detector subsystem 28 may also be protected against environmental influences, such as rain or other environmental conditions by the head 16.

Referring to FIG. 7, in another embodiment, the disclosed system 10 may generally include at least one array 54 of light detectors 24, where an array 54 of light detectors 24 may include at least two light detectors 24, three detectors 24 in each array 54 are shown by example. For example, the system 10 may include a plurality of parallel detectors 24 in order to provide a three hundred and sixty degree (360°) field of view (FOV) and direction of arrival (DOA) capability. In certain embodiments, as illustrated, each detector 24 of the array 54 may include an optic subsystem 26 and a detector subsystem 28 and each array 54 may be connected to and utilize a single, central processor subsystem 30.

Figure 8:
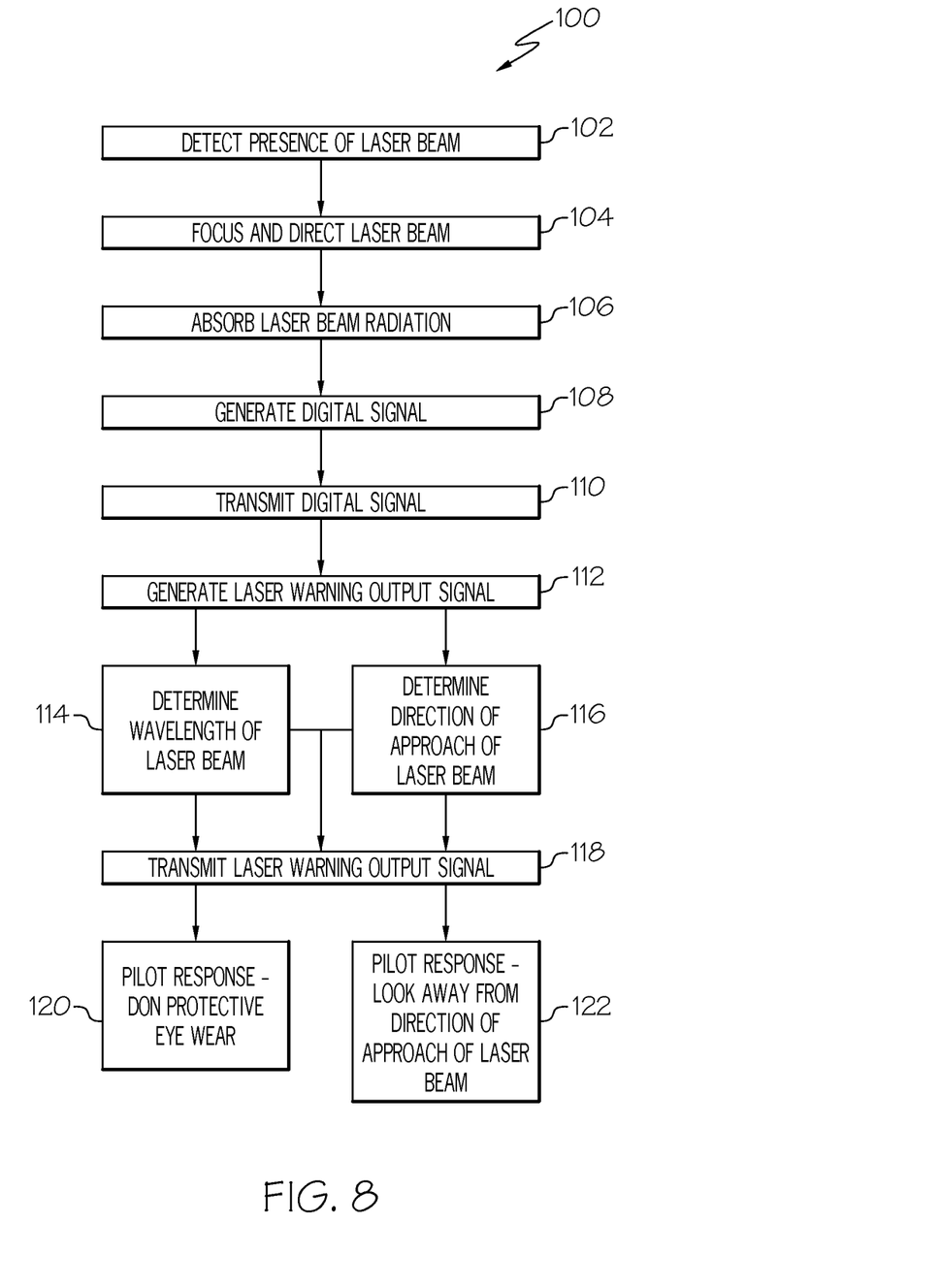
FIG. 8 is a flow chart depicting one embodiment of the disclosed method of warning a pilot of an aircraft of the presence of laser radiation; and, FIG. 9 is a flow chart depicting one embodiment of the disclosed method of determining a location of a source of laser radiation.

Referring to FIG. 8, also disclosed is a method, generally designated 100, for providing a laser warning output signal in response to detection of certain electromagnetic radiation, such as a laser beam. The method 100 may begin at Block 102 with the step of detecting the presence of a laser beam 20 using the disclosed system 10. At Block 104, the laser beam 20 may be focused by the optical subsystem 26 and directed toward the detector subsystem 28. At Block 106, radiation form the laser beam 20 may be absorbed by the detector subsystem 28. At Block 108, a digital signal may be generated in response to the radiation of the laser beam 20. At Block 110, the digital signal may be transmitted by the detector subsystem 28 to the processor subsystem 30 where information related to the laser beam 20 is processed and the laser warning output signal 40 may be provided. At Block 112, the laser warning output signal 40 may be generated, including information about the type of laser beam 20, including the color of the laser beam 20 based on the wavelength of the laser beam 20 (Block 114) and the direction of approach of the laser beam 20 (Block 116). At Block 118, the laser warning signal 40 may be transmitted to the pilot, including indication of appropriate protective eyewear to don and the viewing direction to avoid, and instructions for taking protective measures against the laser radiation. At Blocks 120 and 122, an appropriate pilot response action may then be taken, including donning of appropriate laser safety eyewear in order to shield against the radiation of the identified laser beam 20 to protect the pilot's eyes from damage and prevent flash blindness (Block 120) and avoiding direct view of the identified direction of approach of the laser beam 20 (Block 122).

Figure 9:
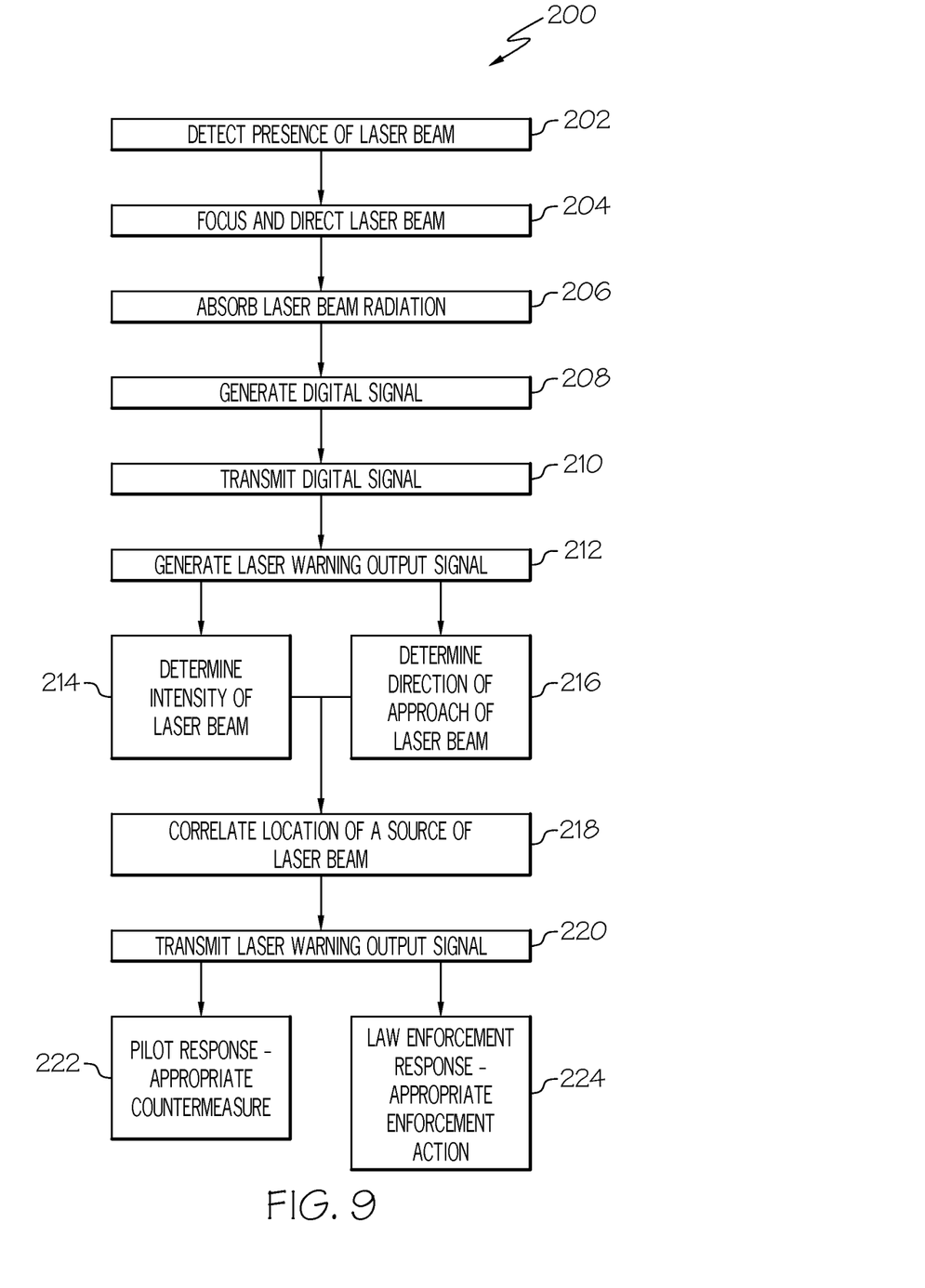

Referring to FIG. 9, also disclosed is a method, generally designated 200, for providing a laser warning output signal 40 in response to detection of a laser radiation, i.e., laser beam 20. The method 200 may begin at Block 202 with the step of detecting the presence of a laser beam 20 using the disclosed system 10. At Block 204, the laser beam 20 may be focused by the optical subsystem 26 and directed toward the detector subsystem 28. At Block 206, radiation form the laser beam 20 may be absorbed by the detector subsystem 28. At Block 208, a digital signal may be generated in response to the radiation of the laser beam 20. At Block 210, the digital signal may be transmitted by the detector subsystem 28 to the processor subsystem 30 where information related to the intensity of laser beam 20 and the direction of approach of the laser beam 20 may be processed and the laser warning output signal 40 may be provided. At Block 212, the laser warning output signal 40 may be generated, including information about the intensity of laser beam 20 (Block 214) and the direction of approach of the laser beam 20 (Block 216). At Block 218, the intensity, i.e., distance, and direction information related to the laser beam 20 may be correlated and processed by the processing subsystem 30 in conjunction with the relative position of the aircraft 12 to determine the location of the source 22 of the laser beam 20. The relative position of the aircraft 12 may be determined by the processing subsystem 30 utilizing GPS coordinates provided by the GPS 46; the pitch, roll, and yaw of the aircraft 12 provided by the navigation processor 48; the position where the system 10 is coupled to the aircraft 12; and the terrestrial location of the aircraft 12 relative to the local area provided by the digital mapping processor 50. At Block 220, the laser warning output signal 40 may be provided, including information about the location of the source 22 of the laser beam 20. At Blocks 222 and 224, an appropriate pilot response (Block 222) or appropriate law enforcement response (Block 224) may be taken based upon the location information provided in the warning signal 40.

It can be appreciated by one skilled in the art that the method 100 described above may be integrated with the method 200 in order to provide a warning signal 40 to the pilot including eye protection and direction of approach information to the pilot for safety and provide location information to law enforcement.

Additionally, in connection with military operations, at Block 222, a digital signal may be transmitted by the detector subsystem 28 to the processor subsystem 30 where information related to the wavelength and modulation frequency of the laser beam 20 is processed. At Block 220, determination of the characteristics of the laser beam 20 may be transmitted to the pilot in the warning signal 40 in order to designate the laser beam 20 as a laser designation or a tracking laser of a surface-to-air missile or air-to-air missile for appropriate countermeasures to be taken by the pilot.

Although various aspects of the disclosed laser detection and warning system have been shown and described, modifications may occur to those skilled in the art upon reading the specification. The present application includes such modifications and is limited only by the scope of the claims.

What is claimed is:

1. A laser detection and warning system comprising:
   a vehicle;
   a detector connected to said vehicle, said detector comprising:
      an optical subsystem configured to collect and focus laser radiation;
      a detector subsystem configured to receive said laser radiation from said optical subsystem and generate a digital signal in response to said laser radiation; and
      a processor subsystem comprising:
         a global positioning system processor configured to provide a location of said vehicle in three-dimensional space;
         a navigation processor configured to provide an orientation of said vehicle in said three-dimensional space;
         a digital ground mapping processor configured to generate a three-dimensional topographic map representing a local area in said three-dimensional space; and
         a digital signal processor configured to:
            determine an azimuth and elevation of said laser radiation relative to said location and orientation of said vehicle; and
            determine a physical location of a source of said laser radiation on said topographic map based on an intersection of a directional projection along said azimuth and elevation and said topographic map.

2. The system of claim 1 wherein said digital signal processor is configured to determine a wavelength of said laser radiation, and wherein said processor subsystem is configured to generate a laser warning output signal indicative of said wavelength of said laser radiation.

3. The system of claim 2 wherein said laser warning output signal provides an indication of a type of eyewear protective against said wavelength of said laser radiation.

4. The system of claim 1 wherein said vehicle is an aircraft.

5. The system of claim 1 wherein said optical subsystem comprises a spectrum filter.

6. The system of claim 1 wherein said detector subsystem comprises a photosensor.

7. The system of claim 1 further comprising a base mounted to said vehicle and a head connected to said base, said head surrounding said detector.

8. The system of claim 7 wherein an array of detectors is disposed within said head configured to provide a three hundred and sixty degree field of view.

9. The system of claim 1 wherein said processor subsystem is configured to generate a laser warning output signal indicative of at least one of a direction of approach of said laser radiation and said location of said source of said laser radiation.

10. A method of warning a pilot of an aircraft of a presence of laser radiation, said method comprising the steps of:
   providing a detector mounted to said aircraft, said detector comprising an optical subsystem, a detector subsystem, and a processor subsystem;
   determining, by a global positioning system processor of said processor subsystem, a location of said aircraft;
   determining, by a navigation processor of said processor subsystem, an orientation of said aircraft;
   generating, by a digital ground mapping processor of said processor subsystem, a three-dimensional topographic map representing a local area;
   collecting, by said optical subsystem, said laser radiation;
   directing, by said optical subsystem, said laser radiation to said detector subsystem;
   generating, by said detector subsystem, a digital signal in response to said laser radiation;
   transmitting, by said detector subsystem, said digital signal to a digital signal processor of said processor subsystem;
   processing, by said digital signal processor, said digital signal to determine a wavelength of said laser radiation and an azimuth and elevation of said laser radiation relative to said location and orientation of said aircraft; and
   determining, by said digital signal processor, a physical location of a source of said laser radiation on said topographic map based on an intersection of a directional projection along said azimuth and elevation and said topographic map.

11. The method of claim 10 further comprising transmitting a laser warning output signal to said pilot, wherein said laser warning output signal indicates a direction of approach of said laser radiation.

12. The method of claim 10 further comprising transmitting a laser warning output signal to at least one of said pilot and law enforcement, wherein said laser warning output signal indicates said location of said source of said laser radiation.

13. The method of claim 10 further comprising transmitting a laser warning output signal to said pilot, wherein said laser warning output signal indicates a type of eyewear protective against said wavelength of said laser radiation.

14. A laser detection method comprising the steps of:
providing a vehicle;
mounting a detector onto said vehicle, said detector comprising an optical subsystem, a detector subsystem, and a processor subsystem;
collecting laser radiation directed at said vehicle by said optical subsystem;
generating a digital signal in response to said laser radiation by said detector subsystem;
determining a location of said vehicle by a global positioning system processor of said processor subsystem;
determining an orientation of said vehicle by a navigation processor of said processor subsystem;
generating a three-dimensional topographic map representing a local area by a digital ground mapping processor of said processor subsystem;
processing said digital signal to determine an azimuth and elevation of said laser radiation relative to said location and orientation of said vehicle by a digital signal processor of said processor subsystem; and
determining a physical location of a source of said laser radiation on said topographic map based on an intersection of a directional projection along said azimuth and elevation of said laser radiation and said topographic map by said digital signal processor.

15. The method of claim 14 wherein said vehicle is an aircraft.

16. The method of claim 14 wherein said step of determining said location comprises referencing topographical data of said local area relative to said location of said vehicle.

17. The method of claim 14 further comprising the step of generating a laser warning output signal when said laser radiation is detected.

18. The method of claim 17 further comprising the step of transmitting said laser warning output signal to law enforcement, wherein said laser warning output signal indicates said location of said source of said laser radiation.

19. The method of claim 17 further comprising the step of transmitting said laser warning output signal to a pilot of said vehicle, wherein said laser warning output signal indicates a direction of approach of said laser radiation.

20. The method of claim 17 further comprising:
processing said digital signal to determine a wavelength of said laser radiation by said digital signal processor; and
transmitting said laser warning output signal to said pilot, wherein said laser warning output signal indicates a type of eyewear protective against said wavelength of said laser radiation.

* * * * *